(12) United States Patent
Minch et al.

(10) Patent No.: US 9,086,400 B2
(45) Date of Patent: Jul. 21, 2015

(54) AMPLIFIER AND ARRAY FOR MEASURING SMALL CURRENT

(75) Inventors: Bradley A. Minch, Plainville, MA (US); Sunitha Bandla Ayers, Ithaca, NY (US); Manfred Lindau, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 1364 days.

(21) Appl. No.: 12/744,891

(22) PCT Filed: Nov. 25, 2008

(86) PCT No.: PCT/US2008/013125
§ 371 (c)(1),
(2), (4) Date: Jan. 24, 2011

(87) PCT Pub. No.: WO2009/073121
PCT Pub. Date: Jun. 11, 2009

(65) Prior Publication Data
US 2011/0121819 A1    May 26, 2011

Related U.S. Application Data

(60) Provisional application No. 60/991,111, filed on Nov. 29, 2007.

(51) Int. Cl.
*G01R 17/00* (2006.01)
*G01R 1/30* (2006.01)
(Continued)

(52) U.S. Cl.
CPC .......... *G01N 33/48728* (2013.01); *G01N 15/10* (2013.01); *G01N 27/403* (2013.01); *G01N 27/49* (2013.01); *G01N 33/487* (2013.01)

(58) Field of Classification Search
CPC ............ G01N 33/48728; G01N 15/10; G01N 27/403; G01N 27/49; G01N 33/487
USPC ........................... 324/123 C, 123 R, 425, 439
See application file for complete search history.

(56) References Cited

U.S. PATENT DOCUMENTS 4,963,815 A * 10/1990 Hafeman .................. 205/777.5
5,608,519 A    3/1997 Gourley et al.
(Continued)

FOREIGN PATENT DOCUMENTS

WO    WO-2009073121 A1    6/2009

OTHER PUBLICATIONS

Hasan, Stability and Compensation Technique for a CMOS Amperometric Potentiostat Circuit for Redox Sensors, Dec. 4-7, 2006, Circuits and Systems, 2006. APCCAS 2006. IEEE Asia Pacific Conference, pp. 876-879.*

(Continued)

*Primary Examiner* — Patrick Assouad
*Assistant Examiner* — Hoang X Nguyen
(74) *Attorney, Agent, or Firm* — Schwegman Lundberg & Woessner, P.A.

(57) ABSTRACT

An array of electrochemical detectors includes an array of electrodes that provide current responsive to oxidation events. Each electrode is coupled to a transistor, an amplifier coupled to an input of the transistor and having a feedback loop coupled to the electrode and providing a bias voltage to the electrode, an integrating capacitor coupled to the transistor operable to integrate charge from the electrode, and a reset switch coupled to the integrating capacitor. The amplifier may have a shared stage with other detectors. A shared buffer circuit may also provide a sampled output from multiple detectors.

25 Claims, 6 Drawing Sheets

(51) Int. Cl.
*G01R 17/16* (2006.01)
*G01R 19/00* (2006.01)
*G01N 27/42* (2006.01)
*G01N 27/02* (2006.01)
*G01N 33/487* (2006.01)
G01N 27/49 (2006.01)
G01N 27/403 (2006.01)
G01N 15/10 (2006.01)

(56) References Cited

U.S. PATENT DOCUMENTS

| | | | |
|---|---|---|---|
| 6,180,415 | B1 | 1/2001 | Schultz et al. |
| 6,654,729 | B1 | 11/2003 | Hickman et al. |
| 6,935,165 | B2 | 8/2005 | Bashir et al. |
| 6,965,407 | B2 | 11/2005 | Boemler et al. |
| 7,015,046 | B2 | 3/2006 | Wohlstadter et al. |
| 7,122,319 | B2 | 10/2006 | Liu et al. |
| 7,201,833 | B2 | 4/2007 | Lauks et al. |
| 7,399,599 | B2 | 7/2008 | Maher et al. |
| 7,428,047 | B2 | 9/2008 | Oldham et al. |
| 8,409,131 | B2 * | 4/2013 | Say et al. ............ 604/65 |
| 2006/0086623 | A1 * | 4/2006 | Narula et al. ............ 205/775 |
| 2007/0105089 | A1 | 5/2007 | Deutsch |
| 2007/0236224 | A1 * | 10/2007 | Augustyniak et al. ........ 324/425 |
| 2010/0066378 | A1 * | 3/2010 | Ahmadi et al. ............ 324/429 |
| 2010/0308796 | A1 * | 12/2010 | Chung et al. .......... 324/123 R |

OTHER PUBLICATIONS

Wu et al., New design techniques for a complementary metal-oxide semiconductor current readout integrated circuit for infrared detector arrays, Jan. 1995, Optical Engineering vol. 34 No. 1, pp. 160-168.*
Wu et al., Focal-Plane-Arrays and CMOS Readout Techniques of Infrared Imaging Systems, Aug. 1997, Circuits and Systems for Video Technology, IEEE Transactions on (vol. 7 , Issue: 4 ), pp. 594-605.*
Minch, A low-voltage MOS cascode bias circuit for all current levels, May 2002, Circuits and Systems, 2002. ISCAS 2002. IEEE International Symposium on (vol. 3 ), pp. 619-622.*
Benini, Luca; Guiducci, Carlotta; Paulus, Christian. "Electronic Detection of DNA Hybridization: Toward CMOS Microarrays". Jan.-Feb. 2007, IEE Design & Test of Computers, vol. 24, Issue 1, pp. 38-48, DOI: 10.1109/MDT.2007.12.*
"International Application Serial No. PCT/US2008/013125, International Search Report mailed Mar. 27, 2009".
"International Application Serial No. PCT/US2008/013125, Written Opinion mailed Mar. 27, 2009".
Albillos, A., et al., "The exocytotic event in chromaffin cells revealed by patch amperometry", *Nature*, 389, (Oct. 2, 1997), 509-512.
Andrew, M., et al., "Amperometric Readout and Electrode Array Chip for Bioeletrochemical Sensors", *IEEE International Symposium*, Circuit and Systems, (May 1, 2007), pp. 3562-3565.
Ayers, S., et al., "Design of a CMOS Potentiostat Circuit for Electrochemical Detector Arrays", *IEEE Transactions on Circuits and Systems I: Regular Papers*, 54(4), (Apr. 2007), 736-744.
Benini, L., et al., "Electronic Detection of DNA hybridzation: Towards CMOS Microarrays", IEEE Design & Test of Computers, IEEE Service Centre, vol. 24, No. 1, New York, NY, US, (Jan. 1, 2007), 38-48 pgs.

Breten, M., et al., "Integrating data converters for picoampere currents from electrochemical transducers", *Circuits and Systems,2000. Proceedings. ISCAS 2000 Geneva*. vol. 5, The 2000 IEEE International Symposium on May 28-31, 2000, Piscataway, NJ, USA, IEEE, (May 28, 2000), 709-712 pgs.
Dernick, G, et al., "Patch amperometry: high-resolution measurements of single-vesicle fusion and release.", *Nat Methods.*, 2(9), (Sep. 2005), 699-708.
Dernick, G. G., et al., "The Patch Amperometry Technique: Design of a Method to Study Exocytosis of Single Vesicles", *Electrochemical Methods for Neuroscience*, A.C. Michael and L.M. Borland, Editors; CRC Press: Boca Raton, FL., (2006), 315-336.
Eversmann, B, et al., "A 128×128 CMOS biosensor array for extracellular recording of neural activity", *IEEE Journal of Solid-State Circuits*, 38(12), (Dec. 2003), 2306-2317.
Frey, A., et al., "Yield Evaluation of Gold Sensor Electrodes Used for Fully Electronic DNA Detection Arrays on CMOS", *Microelectronics Reliability*, 42(9-11), (Sep.-Nov. 2002), 1801-1806.
Genov, R., et al., "16-Channel Integrated Potentiostat for Distributed Neurochemical Sensing", *IEEE Transactions on Circuits and Systems I: Regular Papers*, 53(11), (Nov. 2006), 2371-2376.
Gong, L., et al., "Secretory vesicles membrane area is regulated in tandem with quantal size in chromaffin cells.", *J Neurosci.*, 23(21), (Aug. 27, 2003), 7917-21.
Gore, A., et al., "A Multichannel Femtoampere-Sensitivity Potentiostat Array for Biosensing Applications", *IEEE Transactions on Circuits and Systems I: Regular Papers*, 53(11), (Nov. 2006), 2357-2363.
Hofmann, F., et al., "Fully electronic DNA detection on a CMOS chip: device and process issues", *IEDM '02. Digest. International Electron Devices Meeting*, 2002., (2002), 488-491.
Hsieh, Chih-Cheng, et al., "Focal-plane-arrays and CMOS readout techniques of infrared imaging systems", *IEEE Transactions on Circuits and Systems for Video Technology*, 7(4), (Aug. 1997), 594-605.
Jenkner, M., et al., "Cell-based CMOS sensor and actuator arrays", *IEEE Journal of Solid-State Circuits*, 31(12), (2004), 2431-2437
Jichun, Z., et al., "Electrochemical Array Microsystems With Integrated Potentiostat", *2005 IEEE Sensors*, (Oct. 31, 2005).
Mosharov, E. V, et al., "Analysis of exocytotic events recorded by amperometry", *Nat Methods*, 2(9), (2005), 651-8.
Murari, K., et al., "Integrated potentiostat for neurotransmitter sensing", *IEEE Engineering in Medicine and Biology Magazine*, 24(6), (Nov.-Dec. 2005), 23-29.
Narula, H. S, et al., "A time-based VLSI potentiostat for ion current measurements", *IEEE Sensors Journal*, 6(9), (Apr. 2006), 239-247.
Rezaul, H. S, "Stability Anaysis and Novel Compensation of a CMOS Current—Feedback Potentiostat Circuit for Electrochemical Sensors", *IEEE Sensors Journal IEEE Service Centre*, vol. 7, No. 5, New York, NY, US, (May 1, 2007), 814-824 pgs.
Rezaul, H. S, et al., "Stability and Compensation technique for a CMOS Amperometric Potentiostat Circuit for Redox Sensors", *Circuits and Systems, APCCAS 2006. IEEE Asia Pacific Conference on*, IEEE, Piscataway, NJ, USA, (Dec. 1, 2006), 876-879 pgs.
Wu, Chung-Yu, et al., "New design techniques for a complementary metal-oxide semiconductor current readout integrated circuit for infrared detector arrays.", *Optical Engineering*, 34(1), (Jan. 1995), 160-168.
Wu, Chung-Yu, et al., "New share-buffered direct-injection readout structure for infrared detector", *Proc. SPIE*, vol. 2020, (1993), 57-64.

* cited by examiner

AMPLIFIER AND ARRAY FOR MEASURING SMALL CURRENT

RELATED APPLICATION

This application is a U.S. National Stage filing under 35 U.S.C. §371 from International Application No. PCT/US2008/013125, filed Nov. 25, 2008, published on Jun. 11, 2009 as WO 2009/073121, which claims priority to U.S. Provisional Application Ser. No. 60/991,111 (entitled PIXEL DESIGN OF A SCALABLE LOW-NOISE CURRENT AMPLIFIER ARRAY FOR HIGHLY PARALLEL ELECTROPHSIOLOICAL AND ELECTROCHEMICAL MEASUREMENTS, filed Nov. 21, 2007) which is applications are incorporated herein by reference.

GOVERNMENT FUNDING

This invention was made with Government support under Grant Number ECS-9876771 awarded by NSF and under Grant Number RO1 NSO48826 awarded by NIH. The United States Government has certain rights in the invention.

BACKGROUND

Neuronal function and behavior may be determined, among other mechanisms, by the storage and release of neurotransmitters and hormones. The release of these substances, which are synthesized in the cytosol, occurs by a process of exocytosis, in which a secretory vesicle fuses with the plasma membrane. When an excitable cell is stimulated, the contents of one or more vesicles are released completely into the extracellular space. Release from a single vesicle has been termed quantal release. Techniques used to study quantal release include carbon-fiber amperometry, patch amperometry, and amperometry using microfabricated planar microelectrodes. These amperometric techniques can detect quantal release of oxidizable transmitters, such as the catecholamines epinephrine and norepinephrine, using a carbon fiber or platinum microelectrode that is positioned close to the cell surface and held at a potential that is sufficiently high to oxidize the released molecules. Upon release from a vesicle, the catecholamine molecules that diffuse to the surface of the electrode are rapidly oxidized, resulting in the transfer of two electrons to the electrode. The oxidation of the molecules released in a single quantal event thus generates a transient oxidation current with a duration of a few milliseconds.

DETAILED DESCRIPTION

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

A scalable CMOS biosensor array may be used for the parallel electrochemical detection of individual release events simultaneously from multiple cells with low noise and high temporal resolution.

In one embodiment, a potentiostat or detector circuit is capable of measuring transient amperometric oxidation currents at the surface of an electrode with sub-millisecond time resolution and picoampere current resolution. The potentiostat is a regulated cascode stage in which a high-gain amplifier maintains the electrode voltage through a negative feedback loop. Some embodiments include a shared amplifier structure in which amplifiers in a given row of detectors may share a common half circuit resulting in fewer transistors per detector. In one example embodiment, a chip may be fabricated in a 0.5-μm, 5-V CMOS process through MOSIS (metal oxide semiconductor implementation system).

Each detector in one embodiment occupies a layout area of 35 μm by 15 μm and contains eight transistors and a 50-fF integrating capacitor. The rms current noise at 2 kHz bandwidth is approximately 110 fA. The maximum charge storage capacity at 2 kHz is $1.26 \times 10^6$ electrons.

The oxidation of the molecules released in a single quantal event generates a transient oxidation current with a duration of a few milliseconds. By integrating the transient signal, the number of molecules released can be determined, and is proportional to the quantal size. To understand properties of quantal events and to advance the study of their modulation by drugs, various embodiments described herein provide high-throughput techniques that facilitate measurements of many quantal events from a large number of cells under a variety of experimental conditions.

Figure 1:
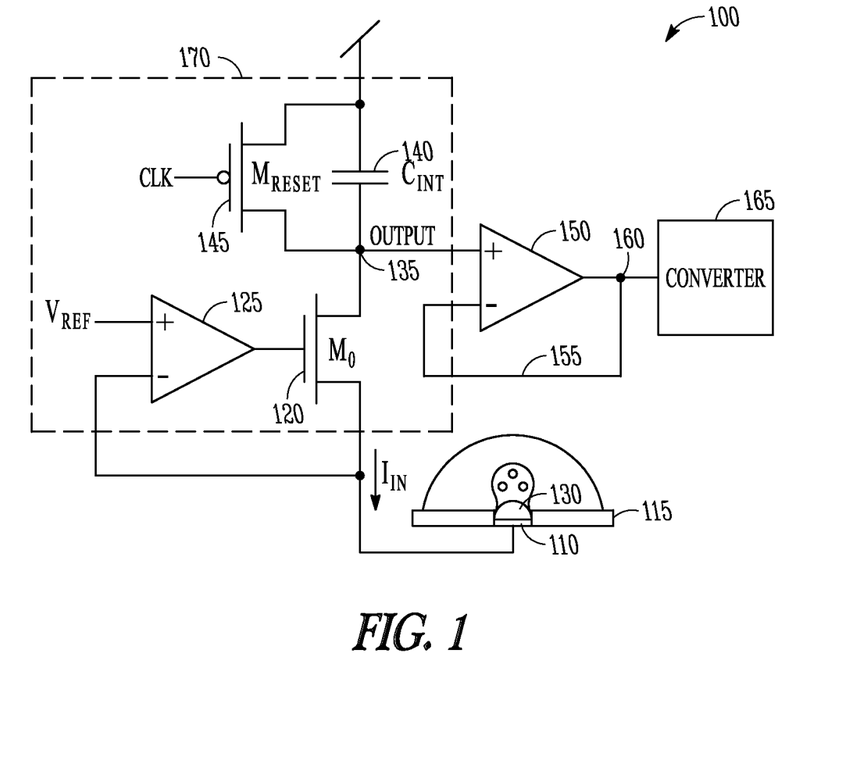
FIG. 1 is a block schematic diagram of a circuit for measuring current according to an example embodiment.

A CMOS electrochemical detector, referred to as a potentiostat detector for characterization of quantal events is shown in FIG. 1 generally at 100. The detector 100 comprises an electrode 110 supported by a substrate 115. The electrode is coupled to a cascode transistor 120 and a feedback amplifier 125 that maintains the electrode 110 at a stable reference voltage, $V_{ref}$. In one embodiment, electrode 110 is a polarizable electrode held at approximately 700 mV and is positioned in close proximity to a cell or other event producing subject. Other voltages may be selected depending on the specific compound to be detected. The operation of the potentiostat is straightforward. The current $I_{in}$, produced as a result of oxidation events 130 on the surface of the electrode 110 surface is converted to an output voltage by current to voltage converter 170. The current $I_{in}$ is buffered by the cascode transistor 120 to the node labeled "Output" 135 where it is integrated by an integration capacitor, $C_{int}$, 140 to produce the output voltage. Periodically, the output voltage is reset to the positive power supply rail, $V_{dd}$, through a reset transistor, $M_{reset}$ 145. In one embodiment, the integrating capacitor 140 has a capacitance of approximately 50-fF.

As the input current, $I_{in}$, is varied, such as from 1 pA to 400 pA, the output voltage varies substantially linearly with the input current. The input impedance of the cascode transistor 120, $g_{s0}$, is relatively low. The addition of a high gain amplifier, such as amplifier 125 producing a regulated cascode 120, the input impedance is further reduced by the gain of the amplifier 120. In this application, a low input impedance is helpful in maintaining a high injection efficiency.

Injection efficiency is defined as the fraction of the electrode current that is buffered by the cascode transistor to the output node. We can show that the low-frequency input impedance of the potentiostat is given by, $$R_{in} = \frac{1}{g_{s0}(1 + \kappa A_0)},\quad (1)$$

where $g_{s0}$ is the incremental source conductance of the cascade transistor $M_0$ 120, $\kappa$ is the reciprocal subthreshold slope factor, a constant with a typical value between 0:5-0:9, and $A_0$ is the low-frequency gain of the regulation amplifier. For a typical input current level of tens to hundreds of picoamperes, this input resistance can be as low as hundreds to tens of kiloohms, which is much less than the impedance of the effective shunt capacitance formed at the liquid-solid interface of the electrode over the frequency range of interest, resulting in a very high injection efficiency.

In one embodiment, the output is coupled to an amplifier 150 having a feedback loop 155 coupled between an output 160 of the amplifier 150 and its inverting terminal. An analog to digital converter 165 may be coupled to the output 160 and may be used to sample the output 160 at the end of an integration time, and convert the integrated voltage level on the capacitor 140 to a digital value. In one embodiment, the converter 165 may be coupled to many different electrodes in an array of electrodes, sampling each one at a desired rate consistent with events on such electrodes. After sampling, switch 145 may be used to remove the accumulated charge on the capacitor 140 and allow it to begin to accumulate charge again during a next oxidation event. In one embodiment, 16-bit A/D converter is clocked externally to sample data at the end of the integration period. The A/D converter is connected to a computer, also represented by block 165 where the data is acquired and analyzed.

In one embodiment, an array of detector units including electrodes and corresponding circuitry may be integrated onto the same substrate 115. Each of the electrodes may be coupled to a regulated cascode amplifier (RCA) such as that illustrated in FIG. 1 at 120 and 125. To achieve cellular dimensions, each detector unit may be on the order of 10-20 μm on a side, which constrains the number of transistors per detector. The electrode potential should be stable, because an unstable electrode voltage leads to charging and discharging of the liquid junction capacitance (generally indicated at 130 in FIG. 1) creating excessive baseline fluctuations in current measurement. The half-width of the release events is typically a few milliseconds, which implies that the readout rate should be at least in the kHz range.

Resulting amperometric spikes are often preceded by a small foot signal of a few picoamperes in amplitude that may contain valuable information on the properties of for example, a fusion pore. This consideration implies that the input-referred noise current of a potentiostat detector should be less than 1 pA. Some CMOS potentiostat designs have been proposed earlier. These designs employ current mirrors to amplify currents to the μA range, increasing power consumption. The RCA detector array is capable of measuring small currents without increasing the power consumption and layout area by eliminating amplifying circuitry. A previous approach involved a pMOS, nMOS OTA (operational transconductance amplifier) and a dual slope comparator. Time-base VLSI (very large scale integration) potentiostats have also been proposed. These designs employ a pF integration capacitor and an OTA that occupies a large area.

In some embodiments of the present invention utilizing a shared amplifier stage, similar performance may be obtained while maintaining a small area for circuitry. In some prior multichannel potentiostat circuits, a standard differential amplifier was used to keep the potential of the electrode constant, while a readout of the current produced from release events was done using a current-mode sigma-delta ADC with a variable oversampling ratio. While these designs are suitable for a small array, some of the embodiments described herein may achieve better spatial resolution with the shared amplifier structure. In one embodiment, an RCA potentiostat may be used for an array that may be fabricated in a 0.5-μm, 5-V CMOS process through MOSIS.

Figure 2:
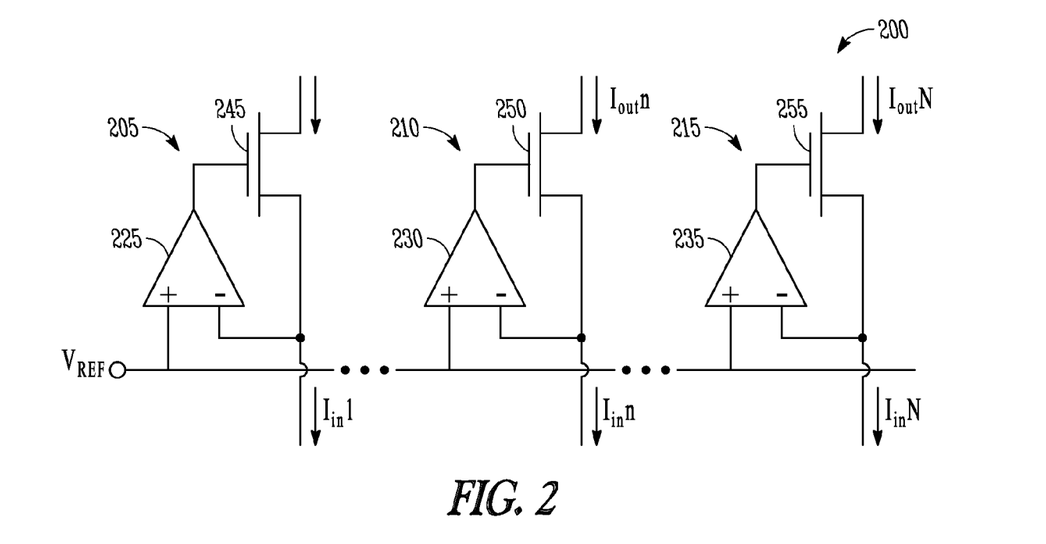
FIG. 2 is block schematic diagram of an array of detectors with separate amplifiers according to an example embodiment.
Figure 3:
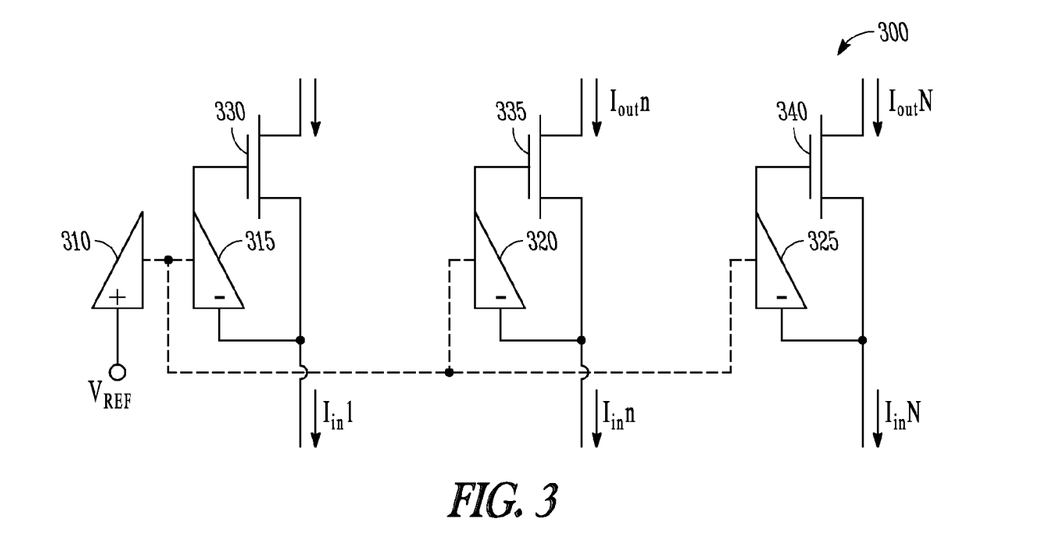
FIG. 3 is block schematic diagram of an array of detectors with separate amplifiers sharing a portion of an amplifier according to an example embodiment.

In order to keep each detector as small as possible, a shared amplifier structure in which all regulation amplifiers in a given row share a common half circuit is used in one embodiment. FIG. 2 shows a one-dimensional array 200 of regulated cascode circuits 205, 210, 215 in which each regulated cascode circuit has its own amplifier 225, 230, 235 coupled to respective cascode transistors 235, 250, 255. However, because the noninverting input of each op-amp in the array is connected to a common potential, $V_{ref}$, a common half circuit among all of the amplifiers in the array may be shared, as shown conceptually in FIG. 3 generally at 300. In amplifier array 300, a non-inverting half 310 of the amplifier is coupled to $V_{ref}$. An inverting half 315, 320, 325, is duplicated for each cascode transistor 330, 335, 340 respectively. In this array topology, each amplifier may be implemented with only approximately half the layout area and approximately half the power consumption as would its counterpart in the array 200 for a given unity-gain bandwidth and low-frequency gain. While three such amplifiers are shown, the dashed lines between them indicate that many more may also be provided and share the non-inverting half 310 in further embodiments. Some form of split amplifier schemes have been used in infrared imaging systems, in which context it is called share-buffered direct injection (SBDI).

Figure 4:
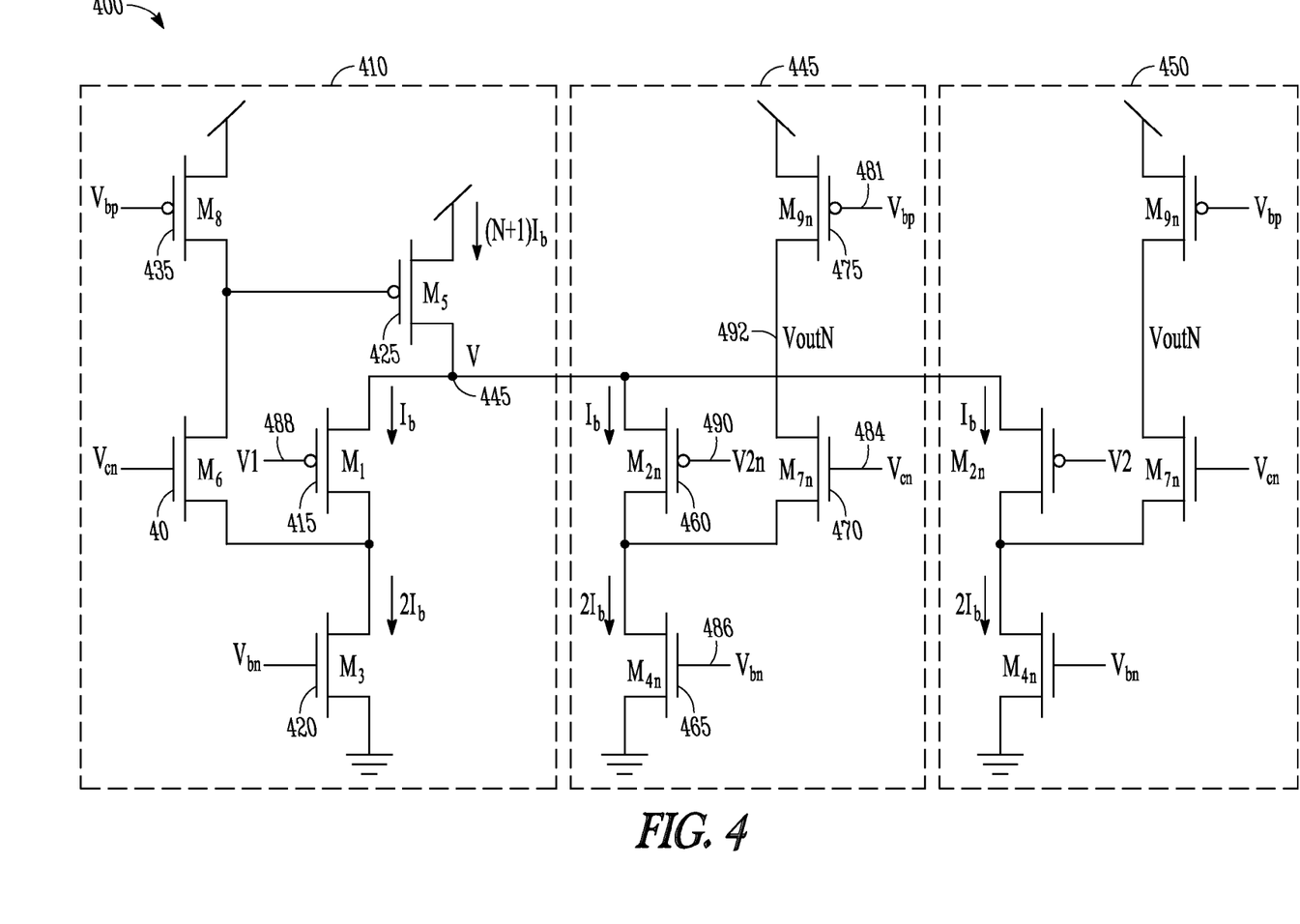
FIG. 4 is block schematic diagram of multiple amplifiers sharing a stage according to an example embodiment.

FIG. 4 illustrates an example transistor-level schematic of a shared amplifier circuit 400 based on a folded-cascode op-amp topology. The shared half circuit (i.e., stage 1, shown with broken line 410) comprises transistors $M_1$ 415, $M_3$ 420, $M_5$ 425, $M_6$ 430, and $M_8$ 435. N independent half circuits (two shown at broken lines 445 and 450) are added to stage 1 410 at a node V at 455. The nth independent half circuit (i.e., stage n) comprises $M_{2n}$ 460, $M_{4n}$ 465, $M_{7n}$ 470, and $M_{9n}$ 475, where n ranges from 1 to N. To generate bias voltages $V_{bp}$ at 481; $V_{cn}$ at 484 and $V_{bn}$ at 486, a low-voltage cascode bias circuit may be used.

The shared half circuit contains a negative feedback loop that maintains V 445 just far enough above a common non-inverting input voltage, $V_1$ at 488, so that transistor $M_1$ passes the bias current, $I_b$.

The operation of a single amplifier is described by considering the shared half circuit, stage 1 410, and the independent half circuit, stage n 445. If the inverting input voltage to stage n 445, $V_{2n}$ at 490, is equal to $V_1$ 488, then transistor $M_{2n}$ 460, which is nominally identical to $M_1$ 415, also passes $I_b$. Consequently, by Kirchhoff's current law (KCL), transistor M$_{7n}$ 470 will also pass I$_b$, which matches the saturation current of M$_{9n}$ 475, so the amplifier will be in its high-gain region in which M$_{7n}$ 470 and M$_{9n}$ 475 are both saturated. If V$_{2n}$ 490 is slightly below V$_1$ 488, then transistor M$_{2n}$ 460 will pass substantially more current than I$_b$, reducing the current flowing in M$_{7n}$ 470 causing V$_{outn}$ 492 to rise until M$_{9n}$ 475 is in its ohmic region. On the other hand, if V$_{2n}$ 490 is slightly above V$_1$ 488, then transistor M$_{2n}$ 460 will pass substantially less current than I$_b$, increasing the current flowing in M$_{7n}$ 470 causing V$_{outn}$ 492 to fall until M$_{7n}$ 470 is in its ohmic region. In a small range of voltages around the point at which, V$_1$ 488 is approximately equal to V$_{2n}$ 490 it can be shown that the incremental output voltage of the shared amplifier is given by, $$\delta V_{out} = A_0(V_1 - V_{2n}) = g_{m2n} r_{o9n}(V_1 - V_{2n}), \quad (2)$$

where A$_0$ is the low-frequency gain of the amplifier, g$_{m2n}$ is the incremental transconductance gain of each input transistor M$_{2n}$, and r$_{o9n}$ is the incremental output resistance of the pMOS transistor M$_{9n}$ 475.

Feedback regulation of node V 445 is done by the N amplifiers that share the common half circuit 410. If the inverting voltages V$_{22}$ through V$_{2N}$=V$_1$, then the inverting input transistors M$_{22}$ through M$_{2N}$, that are equivalent to M$_1$ also pass a current of I$_b$. According to KCL, $$I_5 = I_1 + I_{22} + \ldots I_{2N} = (N+1)I_b. \quad (3)$$

The feedback loop adjusts the gate voltage of M$_5$ 425 to pass a current of (N+1)I$_b$ and the common node V 445 just enough to allow M$_1$ 415 to pass I$_b$. The capacitance at node V 445 is the sum of the N source capacitances contributed by N input stages. Thus the capacitive load on node V 445 is proportional to N. However, from equation (3), the bias current of M$_5$ 425 is also proportional to N.

Shared amplifier 400 represents an improved embodiment over the SBDI circuit, in terms of low-frequency gain, the shared half circuit's ability to drive the capacitive load imposed by the common line V 445; that couples the amplifiers together, and provides stability and isolation between neighboring amplifiers and each amplifier's output swing. Each of these benefits may be provided by various embodiments, and are discussed in the following sections.

Low Frequency Gain

The low frequency gain of amplifier 400 may be given by g$_{m2}$r$_{o9}$. The output impedance and the transconductance gain are provided by different transistors M$_9$ 475 and M$_2$ 460 respectively. The gain of amplifier 400 may be optimized by making the 4 transistor M$_9$ 475 longer. The gain of the amplifier 400 may be a 6 dB improvement over the gain of the SBDI amplifier, which is g$_{m2}$(r$_{o2}$||r$_{o4}$), provided the output impedance of the pMOS and nMOS transistors are comparable. In this circuit, the transconductance gain and the output impedance depend on the same transistor M$_2$. g$_{m2}$ and r$_{o2}$ trade off with each other which would make it difficult to optimize the gain.

Stability and Bandwidth

The negative feedback loop also greatly reduces the incremental resistance through which the half circuit drives node V 445. The incremental resistance seen looking back into the shared half circuit, stage 1, may be given by, $$R_V = \frac{1}{g_{s1}(1 + g_{m5} r_{o8})}. \quad (4)$$

Analysis of the frequency response of the amplifier circuit 400 reveals that the nondominant pole of the amplifier is at node V 445. The nondominant pole is [R$_V$C$_V$]$^{-1}$, where C$_V$ is the total capacitance at node V 445. Due to the reduced impedance given in (6) below, the nondominant pole is pushed farther away from the dominant pole, by the gain (1+g$_{m5}$r$_{o8}$), providing wider bandwidth and stability.

Isolation Between Amplifiers

When there is an incremental change in the input voltage of stage n, $\delta V_{2n}$, and stage (n+1), $\delta V_{2(n+1)}$, an incremental current g$_{m2n}$$\delta V_{2n}$, g$_{m2n}$$\delta V_{2(n+1)}$ flows through M$_{7n}$ 470 and M$_{7(n+1)}$ respectively, changing their output voltages. The incremental output voltages of stages n and (n+1) are, $$\delta V_{outn} = -g_{m2n} r_{o9n}(\delta V_{2n}), \quad (5)$$

$$\delta V_{out(n+1)} = -g_{m2(n+1)} r_{o9(n+1)}(\delta V_{2(n+1)}), \quad (6)$$

The outputs $\delta V_{out(n+1)}$ and $\delta V_{out(n+1)}$ are only dependent on their own input voltages. The node V 445 remains unchanged so long as the noninverting input V1 488 is held constant. The gain from node V 445 to each output of the circuit 400 of FIG. 4 is g$_{s2}$(r$_{o2}$||r$_{o4}$) and to each output of the circuit 400 of FIG. 4 is g$_{s2}$r$_{o9}$. Any movement of node V 445 induced by the inverting input of one amplifier would couple into the other outputs. The common source line, V 445, is better regulated by the negative feedback loop, which lowers the effective resistance through which V 445 is driven by a factor of g$_{m5}$r$_{o8}$.

Output Swing

Many previous applications vary the reference voltage to observe redox currents at the electrode surface. With some of the shared amplifier embodiments described herein, the potential of the electrode may be set anywhere in the range of 0V to 3:2 V. The output swing of the amplifier 400 extends approximately from two saturation voltage drops above ground to one saturation voltage drop short of V$_{dd}$. In subthreshold, the saturation voltage drop is approximately 100-130 mV, which translates to an almost rail-to-rail output voltage swing. Circuit 400 may be used to regulate both pMOS and nMOS transistors without loosing output swing.

The shared amplifier topologies allow achievement of performance similar to a folded-cascode amplifier at a cost of fewer than half the number of transistors in each potentiostat. The amplifier can have a low-frequency gain in the thousands and effectively maintain a stable reference voltage at each electrode.

Noise Analysis

Figure 5:
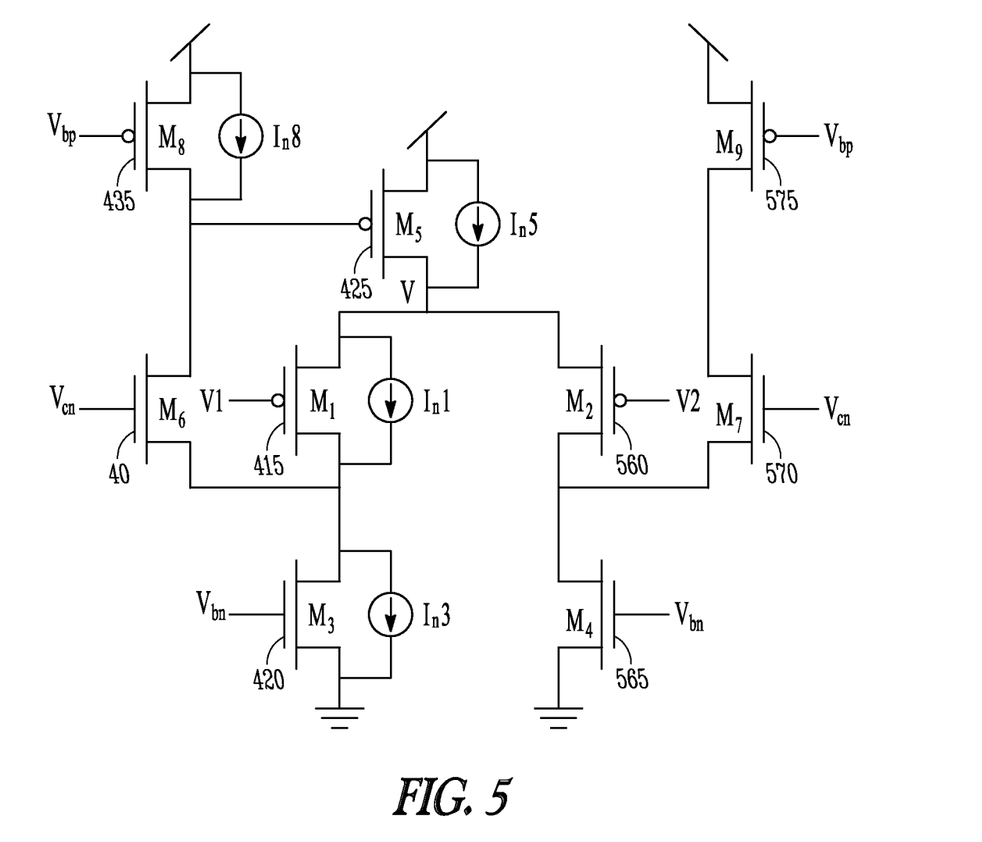
FIG. 5 is a block schematic diagram illustrating thermal noise sources of the amplifier of FIG. 4 according to an example embodiment.

The noise performance of amplifier 400 may be comparable to that of a folded-cascode amplifier, for a given bias level and set of transistor dimensions. The thermal noise sources corresponding to each transistor of our amplifier are shown at 500 in FIG. 5. These sources represent the thermal current noise per unit bandwidth of a subthreshold MOS transistor, the variance of which is given by:

$$\overline{i_n^2} = \frac{2kT}{\kappa} g_m, \quad (7)$$

where the transconductance g$_m$=κI$_D$/U$_T$ and κ is the reciprocal subthreshold slope factor. The inverting half of amplifier 400 is similar to that of a regular folded cascode amplifier, resulting in the same effect by each corresponding transistor on the output node. It can be shown that the corresponding transistors in the non-inverting half of the amplifiers have a similar effect on their output nodes. The noise current source i$_{n5}$ sees a current divider between the two paths. The numbering of the first stage transistors is the same in FIG. 5 as in FIG. 4. Since only a second stage is shown, new reference numbers are used for the transistors in the second stage. The second stage contains transistors 560, 565, 570, 575, and $V_{out}$ 592.

The output thermal noise contribution of transistor $M_5$ 425 is $i_{no5}$, given by, $$i_{no5} = \frac{i_{n5}}{g_{m5}r_{o8} + 2}.$$

For typical bias currents, the loop gain $g_{m5}r_{o8} \gg 1$. Further, when the amplifier is shared among N electrodes in a row, $g_{m5}r_{o8}$ is larger. Since $g_{m5}$ is proportional to bias current, which is $(N+1)I_b$, the loop gain $g_{m5}r_{o8}$ is increased N-fold.

The increase in $g_{m5}$ also leads to an N-fold increase in the noise current source $i_{n5}$. However, the resulting noise current is shared by N half-amplifiers contributing negligible noise currents to each amplifier's output. Thus, it may be concluded that $i_{no5}$ is negligible. The effect of noise source $i_{n8}$ on the output is $$i_{no8} = i_{n8}\frac{g_{m5}r_{o8}}{g_{m5}r_{o8} + 2} \approx i_{n8}.$$

Similarly the effect of $M_3$ 420 is, $i_{no3} \approx i_{n3}$: complete noise analysis reveals that the total input referred voltage noise per unit bandwidth, $\overline{v_{ni}^2}$ is, $$\overline{v_{ni}^2} = \frac{4kT}{\kappa}\left(\frac{1}{g_{m1}} + \frac{g_{m3}}{g_{m1}^2} + \frac{g_{m8}}{g_{m1}^2}\right). \tag{8}$$

The input referred noise is approximately equal to that of a folded cascode amplifier, although in amplifier 400, the amplifier occupies approximately half the layout area and consumes approximately half the power per amplifier.

Flicker (or 1/f) noise is an important consideration in low frequency measurements. In most CMOS technologies, Pmos transistors have one or two orders of magnitude lower 1/f noise than do nMOS transistors. In amplifier 400, by using pMOS input transistors, we reduced the 1/f noise. Flicker noise is inversely proportional to the gate area. Maximizing the area of the transistors, however, would increase the pitch. Here, the choice of minimum width transistors degraded the 1/f noise. The 1/f noise may be further reduced by using a correlated double sampling circuit, described with respect to FIG. 6 below.

In addition to the noise contributed by the feedback amplifier, the reset transistor $M_{reset}$ 145 contributes noise due to clock feedthrough, charge injection and thermal noise of the on resistance of the reset switch. When the signal goes from on to off i.e. from low to high, the clock signal feeds through the gate-drain capacitance $C_{gd}$, and appears across the integration capacitance $C_{int}$. The clock feedthrough may be quantified as, $$v_{nclk} = \frac{C_{gd}V_{dd}}{C_{gd} + C_{int}}. \tag{9}$$

Another form of noise due to the reset transistor 145 is charge injection. When the switch is turned off, the charge under the gate oxide is injected into the integration capacitor. However, these effects are offsets and can be corrected through calibration and double sampling. The on-resistance of the switch introduces thermal noise on the output node and when the switch is turned off, this noise is sampled onto the integration capacitor. This noise scales as, $$\overline{v_{nth}^2} = \frac{kT}{C_{int}}. \tag{10}$$

It can be reduced by increasing the integrating capacitor which would also increase the layout area and decrease the transimpedance gain for a given switching frequency. We have to optimize the size of the integration capacitor considering the trade off between noise, layout area, frequency and gain.

Output Stage

The source follower, which is used to buffer the detector output to the readout circuitry in infrared imagers and active pixel sensors, suffers from many shortcomings. The source follower has limited output voltage swing. The gain of the source follower is κ, which has a dependence on its input voltage, so the source follower is nonlinear. The temperature dependence of κ and the back-gate effect also degrade the gain. However, the source follower is widely used because of its simplicity and smaller layout area. Amplifier 400 is an almost rail-to-rail differential amplifier that has uniform gain of unity across the chip. A schematic of the first row of potentiostat detector circuits and the common output stage is shown at 600 in FIG. 6.

Figure 6:
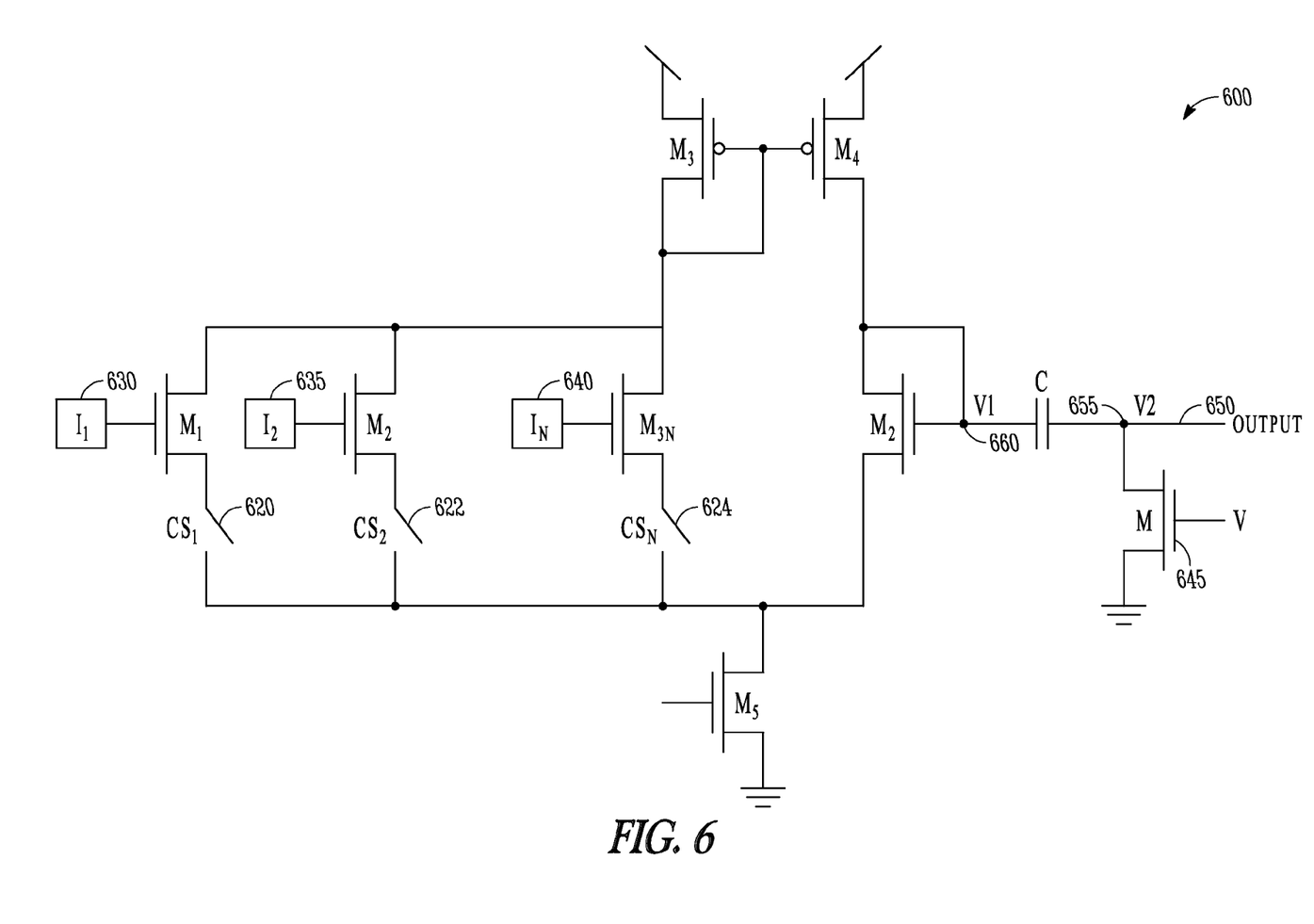
FIG. 6 is a block diagram of a shared output buffer for multiple detectors according to an example embodiment.

In FIG. 6, a block diagram of a common output buffer generally at 610. Output buffer 610 is shared by n columns in an array. Each column is sequentially switched through switches 620, 622, 624, etc., to output buffer 610. The buffer 600 is shared by all the detectors in a row. The detectors 11 through 1n, identified by reference numbers 630, 635, 640 are sequentially switched to complete the buffer by turning on the column switches cs1 through csn, 620, 622, 624. The noninverting input and the access switch are a part of the detector, while the remaining transistors are outside the detector. By using this architecture, we achieve better performance than the source follower without paying in terms of layout area. A buffered output 650 is then fed to a correlated-double sampling (CDS) circuit.

At the end of the integration period, a clamping transistor $M_{clamp}$ at 655 and cs1 620 are closed. Node $V_1$ at 660 is set to a voltage of $(V_{dd}-V_{sig}+V_n)$, where $V_{sig}$ the output voltage of potentiostat/detector 11 630, and $V_n$ is the 1/f noise. During this time, $V_2$ at 665 is held at ground by $M_{clamp}$ 655. At reset, when the integrating capacitor $C_{int}$ is reset to $V_{dd}$, the switch $M_{clamp}$ 655 is opened pulling $V_1$ to $(V_{dd}+V_n)$. The voltage $V_2$ at 665 is the difference of the two samples, $(V_{dd}+V_n)-(V_{dd}-V_{sig}+V_n)=V_{sig}$, which is buffered onto a multiplexed common bus. The CDS circuit thus reduces the 1/f noise. In one embodiment, transistor $M_5$ 425 sets the bias current that flows in the readout amplifier. Transistors $M_3$ 420 and $M_4$ 565 constitute a pMOS current mirror that causes the current flowing in the output branch (i.e., the one on the right) of the readout amplifier to equal the current flowing in the selected input branch (i.e., the one on the left), which makes the output voltage equal to the selected pixel voltage.

Figure 7:
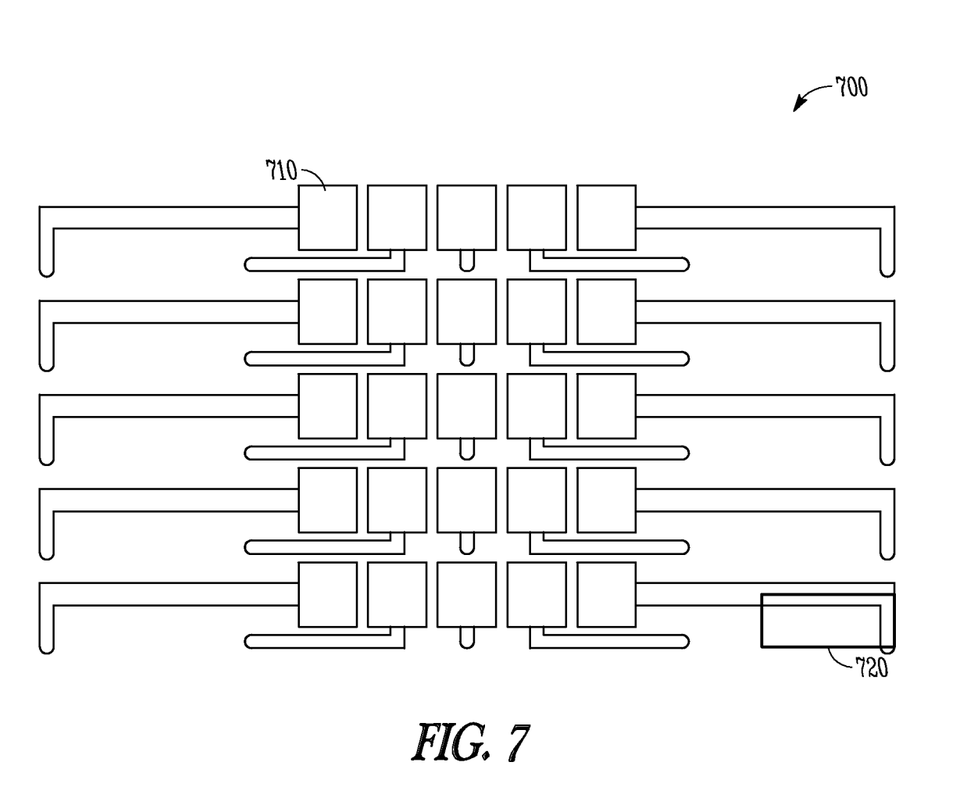
FIG. 7 is a microgram of an array of detectors formed on a die according to an example embodiment.

In one embodiment, a test chip containing a 5×5 detector array was produced using a 0:5-μm, 5-V CMOS process through MOSIS, and is shown at 700 in a micrograph in FIG. 7. The area of a single detector was 525 μm2 and the pitch was 15 μm. The electrodes, are arranged in rows an columns of five, one of which is indicated at 710. In one embodiment, the electrodes are 10µ on each side. The area enclosed by a solid line rectangle 720 is a single potentiostat/detector circuit.

The CMOS industry generally uses copper or aluminum for metal layers. An electrode formed using CMOS processes may be modified to allow for electrochemical detection. A first step of post processing of a CMOS chip involves fabricating polarizable electrodes on the chip to measure amperometric signals.

When a polarizable electrode is immersed in salt solution, no current flows through the electrode-liquid interface. When a voltage is applied to the polarizable electrode, excess charge accumulates on the electrode surface, and is counter balanced by the ionic charge in the solution at a finite distance called the Debye length. Current does not flow through the interface at equilibrium. However, when oxidizable molecules diffuse to the surface of the electrode, electrons are transferred. Typical polarizable electrode materials include carbon, platinum and gold. Patterning metal layers using photolithography is a widely used method for post CMOS fabrication. However, it may be difficult to handle small CMOS dies through the various stages of the fabrication process. On small CMOS dies platinum can be easily deposited using the focused electron beam technique.

The native oxide layer on aluminum may be milled away using the focused electron beam. A directional flow of gas over the chip interacts with the electron beam depositing platinum on the electrode surface. However, the deposited platinum contains impurities. The composition of the deposited layer in one embodiment may be platinum:carbon:gallium:oxide=45:24:28:3, and the resistivity is 70-700 µΩ-cm. The resistivity of gold is 2.2 µΩ-cm and platinum is 10 µΩ-cm. The increased resistivity of the transducer may lead to higher noise levels.

Impurities in the focused electron beam deposited film may arise from the interaction between the electron beam and the sample, the beam current, and grounding of the sample. At low beam currents, penetration of the impurities is minimized.

In a further embodiment, platinum may be deposited over aluminum electrode pads of the chips fabricated at MOSIS using a focused ion beam. The focused ion beam is a direct write instrument that is often used to correct CMOS integrated circuits. This technique may be used to remove native oxide on the aluminum pads and then deposit platinum.

In further embodiments, physical vapor deposition of ti/au may be used to form polarizable electrodes during post fabrication of a CMOS die. To allow proper handling, the CMOS die is mounted on a 4" wafer and the photoresist (such as Shipley 1813) is spun. The photoresist is then patterned using photolithography exposing only the areas over the aluminum pads and developed. Photoresist spins off of the edges of the small CMOS die due to its rectangular shape, the edges of the chip are initially not covered with photoresist. Therefore additional photoresist may be manually applied to the edges of the CMOS die and hard baked.

The chip is then descummed in an electron-free mode (to prevent damage due to ion interactions) to remove the native oxide and organic materials. The metal (Pt or Au) is vapor deposited followed by a lift-off process of the remaining photoresist covered with metal leaving behind only the metal in direct contact with the die surface, which forms the electrode surface.

The CMOS die is then wire bonded to a dual-inline plastic package with a cut-out that exposes the surfaces of the CMOS die and the wiring connections. The whole area is subsequently covered with epoxy (Devcon 5 minutes) to protect the sensitive bonding pads, wire bonds and connecting wires from contact with the electrolyte solution. In one embodiment, only the central part of the chip (indicated by the green square) is left open exposing the electrochemical detector electrodes. The layout of the chip may be designed such that the electrochemical detectors are positioned in the center of the chip, spatially well separated from the I/O pads and wire bonds to ensure the epoxy covering the connections is not flowing over the active electrodes.

In a further embodiment, a modified layout of a chip with the electrode pads having larger separation distances may be fabricated. Gold, which is a polarizable electrode material, may be deposited on the aluminum pads using photolithography. Larger pads at the periphery of the chip may be used as I/O pads. The I/O pads and wires connecting the pads to the package may be isolated from the bath solution using epoxy. Inner electrode pads may be exposed to the solution.

A well formed by a cut out in the plastic package may be filled with electrolyte solution. A picospritzer device or microfluidic channels may be used to eject pico liter amounts of buffer containing various concentrations of dopamine from a micropipette onto such an electrode. An Ag/AgCl ground electrode may be placed inside the ejection pipette or fabricated on the chip.

To measure cellular exocytosis on chip, cells may be positioned on the electrode and stimulated. In one experimental embodiment, an upright Ziess Axioskop microscope may be used to position the cells. The working distance at higher magnification may not allow manipulation of cells using a micropipette. To overcome this problem, a wide-mounted pipette approximately 100-200 µm may be filled with chromaffin cells in physiological saline may be positioned close to the electrodes. Gentle pressure may be applied allowing the cells to settle randomly on the electrode. A small volume of a solution containing the calcium ionophore ionomycin at 20 µM concentration may be pipetted or otherwise applied onto the chip and amperometric currents may be recorded. Not all electrodes may have a cell settling on them using this method, so results may vary significantly.

CONCLUSION

A large number of drugs target ion channels. Pre-clinical drug testing is needed to test new drugs on their effects on ion channel function. Patch-clamp arrays may allow automated electrophysiological measurements from several cells at the same time but no suitable amplifier technology exists to perform economical multichannel recordings from hundreds of cells. Some of the embodiments described herein may provide a very small very low cost solution based on a minimal number of transistors, to incorporate amplifier arrays into highly parallel patch clamp array devices. A second important area is the drug modulation of hormone and transmitter release. In response to specific signals, many cell types release pre-formed molecules that are packaged into secretory vesicles, by fusion with a plasma membrane. This process is called exocytosis and the contents of a single vesicle are released as a unit or quantum with quantal size being the response produced by the molecules released from a single vesicle. The released molecules are oxidizable and hence, can be measured as currents. Analysis of these currents reveals the number of molecules released per vesicle (quantal size) and the time course of release. These parameters are affected by many drugs. For example, the drug L-DOPA, used to treat Parkinson's disease increases quantal size while amphetamines decrease quantal size.

Botulinum toxin A, a partial inhibitor of neurotransmitter release, was approved in 1989 by the US Food and Drug Administration (FDA) for the treatment of strabismus, blepharospasm, and focal spasms including hemifacial spasm and more recently for treatment of cervical dystonia. There is thus considerable need for a better understanding of the mechanisms of these treatments based on a detailed understanding of the molecular mechanisms of transmitter release and its regulation.

Currently many drug effects on transmitter release from single vesicles are being discovered. Such measurements usually require carbon fiber microelectrode recordings from single cells under a microscope. There is no technology available at present to record simultaneously from large numbers of cells. Various embodiments described herein may provide microchip electrode arrays that record single release events from a large number of cells without the need of microscopic manipulation and will allow rapid collection of date to test statistical significance.

A third area where various embodiments may be useful is the are of electrochemical detection of biomolecules through the use of enzymes such as oxidases and dehydrogenases. For high-throughput testing in medical diagnostics, biodefense applications and environmental testing simultaneous multi-channel recordings from hundreds of samples are needed. These employ basically the same amperometric detection techniques but enable specific detection of various analytes by surface modification of individual electrode sensors on the array.

A fourth application is to adapt the embodiments to perform voltammetric rather than amperometry employing time-dependent voltage signals applied to the amplifier reference potential.

Various embodiments incorporating the arrays for a scalable low-noise current amplifier for highly parallel electrophysiological and electrochemical measurements makes possible a high-throughput device, which will be able to record simultaneous bioelectric currents from hundreds of cells or other biological samples. This device will be useful in high throughput drug testing on ion channel function, transmitter release, and chemical testing. It can be applied in pre-clinical drug-testing, medical diagnostics, biodefense devices, and environmental testing.

The present scalable low-noise current amplifier for highly parallel electrophysiological and electrochemical measurements is the first device designed to record currents from hundreds of cells or other samples at the same time. Every electrode may have its own amplifier and the size of the pixel is comparable to most cells, minimizing the size and cost of the apparatus.

Various embodiments may provide improvements and contributions, including new integrating current amplifier architecture that accounts for a compact pixel with the dimensions of a typical cell. Amplifiers may be arranged in a 2-dimensional array, which enables recordings from hundreds of cells for the first time. Reduced size and cost of apparatus for highly parallel measurements of bioelectric currents in patch-clamp and other applications may also result from the use of various embodiments. Some embodiments may be viable for highly parallel simultaneous patch-clamp recordings form hundreds of cells for drug testing and research, highly parallel simultaneous amperometric recordings of release of oxidizable hormones and neurotransmitters form hundreds of cells for drug testing and research, highly parallel simultaneous testing for pathogens using electrochemical detection of pathogens, highly parallel simultaneous testing of hundreds of substances using electrochemical detection in medical diagnostics, and/or highly parallel simultaneous measurements of hundreds of substances using electrochemical detection in environmental testing.

The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims.

The invention claimed is:

1. A device comprising:
a substrate;
an array of biological cell-sized detector electrodes supported by the substrate including plurality of biological cell-sized detector electrodes paired with one reference electrode;
circuitry supported by the substrate and integrated with the array of electrodes configured to measure transient amperometric oxidation currents from the electrodes and including multiple amplifiers formed with a shared half circuit and a non-shared half circuit, wherein the non-shared half circuit of each amplifier is associated with each electrode and the shared half circuit comprises a non-inverting half of the amplifiers and includes a folded cascode amplifier.

2. The device of claim 1 wherein the circuitry comprises an amplifier and an integrating capacitor for each electrode in the array.

3. The device of claim 2 wherein the amplifier has a feedback loop to bias each electrode at a desired reference voltage.

4. The device of claim 2 wherein the integrating capacitor further comprises a switch for draining charge from the capacitor at desired times.

5. The device of claim 1 wherein the folded cascode amplifier of the shared half circuit is configured to provide a large output voltage swing and provide a low input impedance.

6. The device of claim 1, wherein the non-shared half of each amplifier is a folded cascode amplifier having an output voltage range that is substantially rail to rail.

7. The device of claim 1 wherein the circuitry comprises a current to voltage converter.

8. The device of claim 7 wherein the current to voltage converter is integrating or non-integrating.

9. The device of claim 1 wherein the array comprises at least 25 amplifiers and 25 electrodes.

10. The device of claim 1, wherein a side dimension of a biological cell-sized polarizable detector electrode is included in a range of five to twenty micrometers (5-20 μm).

11. A device for measuring current, the device comprising:
a cascode transistor for coupling to an input electrode;
an amplifier coupled to an input of the cascode transistor and having an external feedback loop for coupling to the electrode and providing a bias voltage to the input electrode, wherein the amplifier comprises a split amplifier comprising a first shared input stage, multiple second input stages, and an output stage common to the shared first input stage and multiple second input stages, wherein the first shared input stage includes an internal feedback loop electrically coupled to a circuit node common to the shared first input stage and multiple second input stages;
an integrating capacitor coupled to the cascode transistor for integrating charge from the input electrode; and
a reset switch coupled to the integrating capacitor.

12. The device of claim 11 wherein the device is formed on a single chip having an opening for the input electrode.

13. The device of claim 11 wherein the shared input stage is included in a non-inverting half of the split amplifier and wherein the non-inverting half of the split amplifier functions as an error amplifier.

14. An array of electrochemical detectors comprising:
an array of detector electrodes that provides current responsive to oxidation events, wherein a plurality of detector electrodes is paired with one reference electrode, and wherein each detector electrode is biological cell-sized and coupled to:
  a transistor;
  a split amplifier coupled to an input of the transistor and having a feedback loop coupled to the electrode and providing a bias voltage to the detector electrode, wherein the split amplifier includes a shared half circuit and a non-shared half circuit, wherein the non-shared half circuit is associated with each electrode and the shared half circuit comprises a non-inverting half of the split amplifier and includes a folded cascode amplifier circuit;
  an integrating capacitor coupled to the transistor operable to integrate charge from the detector electrode; and
  a reset switch coupled to the integrating capacitor.

15. The array of claim 14 wherein multiple electrodes share a first half of the amplifier.

16. The array of claim 15 wherein electrodes in a row of the array share the first half of the amplifier.

17. The array of claim 15 wherein the first half of the amplifier is a non-inverting half of the amplifier.

18. The array of claim 15 wherein each electrode has a dedicated second, inverting half of the amplifier.

19. The array of claim 14 wherein the amplifier distributes thermal noise of the shared first half of the amplifier among dedicated second inverting halves of the amplifier of the electrodes.

20. The array of claim 14 wherein the amplifier comprises a regulated cascode amplifier.

21. A shared amplifier array comprising:
a first shared non-inverting amplifier stage coupled to a reference voltage; and
multiple second inverting amplifier stages sharing the first shared non-inverting amplifier stage, the inverting amplifier stages formed in a folded cascode arrangement such that it provides a substantially rail to rail output voltage,
wherein the first shared non-inverting amplifier stage includes a feedback loop that lowers an impedance at a circuit node that electrically couples the first shared non-inverting amplifier stage and the multiple second inverting amplifier stages, and wherein an output of a second inverting amplifier stage is electrically coupled to a cascode transistor which is for coupling to an input electrode.

22. The shared amplifier array of claim 21 wherein the feedback loop biases the circuit node relative to a voltage at an input of the first shared non-inverting amplifier stage.

23. The shared amplifier array of claim 21 wherein the first non-inverting amplifier stage includes a negative feedback loop and functions as an error amplifier.

24. A current detector array comprising:
a plurality of detectors, each having a detector electrode biological cell-sized for providing current from oxidation events, a split amplifier for biasing the detector electrodes to a reference voltage, a cascode transistor, and an integrating capacitor, wherein the split amplifier includes a shared half circuit and a non-shared half circuit, wherein the non-shared half circuit is associated with each electrode and the shared half circuit comprises a non-inverting half of the split amplifier and includes a folded cascode amplifier;
a shared output buffer circuit; and
a switch coupled to each detector for alternately switching each of the detectors to the shared output buffer circuit, wherein a plurality of detector electrodes of the plurality of detectors is paired with one reference electrode.

25. A method comprising:
distributing multiple small current producing entities across a substrate having an array of detector electrodes biological cell-sized and supported by the substrate and circuitry supported by the substrate and integrated with the array of detector electrodes configured to measure transient amperometric oxidation currents from the electrodes using multiple amplifiers formed with a shared half circuit and a non-shared half circuit, wherein the non-shared half circuit of each amplifier is associated with each electrode and the shared half circuit comprises a non-inverting half of the amplifiers and includes a folded cascode amplifier; and
measuring current produced by the current producing entities at each electrode in the array of electrodes.

* * * * *